US009616144B2

(12) United States Patent
Shannon et al.

(10) Patent No.: US 9,616,144 B2
(45) Date of Patent: *Apr. 11, 2017

(54) FOOD-HANDLING FACILITY DISINFECTION TREATMENT (75) Inventors: Michael Edward Shannon, Picton (CA); Dick Eric Zoutman, Kingston (CA)

(73) Assignee: Medizone International Inc., Stinson Beach, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 13/821,483

(22) PCT Filed: Sep. 8, 2011

(86) PCT No.: PCT/CA2011/050544
§ 371 (c)(1),
(2), (4) Date: Mar. 7, 2013

(87) PCT Pub. No.: WO2012/031366
PCT Pub. Date: Mar. 15, 2012

(65) Prior Publication Data
US 2013/0164385 A1    Jun. 27, 2013

Related U.S. Application Data (60) Provisional application No. 61/380,758, filed on Sep. 8, 2010.

(51) Int. Cl.
*A61L 2/20* (2006.01)
*A01N 59/00* (2006.01)
(Continued)

(52) U.S. Cl.
CPC .......... *A61L 2/202* (2013.01); *A01M 1/2022* (2013.01); *A01M 13/00* (2013.01); *A01N 59/00* (2013.01);
(Continued)

(58) Field of Classification Search
CPC ............. A61L 2/20; A61L 2/202; A61L 2/208
See application file for complete search history.

(56) References Cited

U.S. PATENT DOCUMENTS 5,316,741 A    5/1994 Sewell et al.
5,666,640 A    9/1997 Daniylchev
(Continued)

FOREIGN PATENT DOCUMENTS

CA    2473540 A1    7/2003
CA    2486831    2/2004
(Continued)

OTHER PUBLICATIONS

Influence of Catalase and Superoxide Dismutase on Ozone Inactivation of Listeria monocytogenes. Fisher et al. Applied and Environmental Microbiology Apr. 200, p. 1405-1409.*
(Continued)

*Primary Examiner* — Sean E Conley
*Assistant Examiner* — Donald Spamer
(74) *Attorney, Agent, or Firm* — Durham Jones & Pinegar, P.C. Intellectual Property Law Group (57) ABSTRACT Food handling facilities such as meat packing, plants, dairies, kitchens and the like are disinfected using a disinfecting atmosphere which includes ozone and hydrogen peroxide, at a relative humidity of at least 60%.

19 Claims, 4 Drawing Sheets (51) Int. Cl.
A01M 1/20 (2006.01)
A01M 13/00 (2006.01)
A61L 2/24 (2006.01)
A61L 9/015 (2006.01)

(52) U.S. Cl.
CPC ............... *A61L 2/208* (2013.01); *A61L 2/24* (2013.01); *A61L 9/015* (2013.01); *A61L 2202/13* (2013.01); *A61L 2202/14* (2013.01); *A61L 2202/16* (2013.01); *A61L 2202/25* (2013.01); *A61L 2209/211* (2013.01); *A61L 2209/212* (2013.01)

(56) References Cited

U.S. PATENT DOCUMENTS

| | | | | |
|---|---|---|---|---|
| 6,027,572 | A | * | 2/2000 | Labib .................. A61C 1/0076 134/22.12 |
| 6,045,846 | A | | 4/2000 | Bautista et al. |
| 7,217,685 | B2 | | 5/2007 | McDonnell et al. |
| 7,393,818 | B2 | | 7/2008 | McDonnell et al. |
| 7,407,624 | B2 | | 8/2008 | Cumberland et al. |
| 8,551,399 | B2 | | 10/2013 | Shannon et al. |
| 8,636,951 | B2 | | 1/2014 | Shannon et al. |
| 8,992,829 | B2 | | 3/2015 | Shannon et al. |
| 2003/0039729 | A1 | | 2/2003 | Murphy et al. |
| 2003/0132279 | A1 | | 7/2003 | Stemmle |
| 2004/0003511 | A1 | | 1/2004 | Silver |
| 2005/0129571 | A1 | | 6/2005 | Centanni |
| 2005/0226764 | A1 | | 10/2005 | Moirandat et al. |
| 2006/0104858 | A1 | | 5/2006 | Potember et al. |
| 2007/0079455 | A1 | | 4/2007 | Brewer et al. |
| 2007/0086914 | A1 | | 4/2007 | Antinozzi |
| 2008/0031770 | A1 | | 2/2008 | Heselton et al. |
| 2009/0047174 | A1 | | 2/2009 | Hill |
| 2009/0263499 | A1 | | 10/2009 | Platt, Jr. et al. |
| 2012/0020832 | A1 | * | 1/2012 | St. Onge .................. A61L 9/015 422/4 |

FOREIGN PATENT DOCUMENTS

| | | |
|---|---|---|
| CA | 2491781 A1 | 7/2005 |
| CA | 2547589 | 7/2005 |
| CA | 2526367 A1 | 4/2007 |
| WO | 2004011041 | 2/2004 |
| WO | 2005060385 | 7/2005 |
| WO | 2009046562 | 4/2009 |
| WO | 2011003179 | 1/2011 |
| WO | 2011085466 | 7/2011 |

OTHER PUBLICATIONS

Canadian Intellectual Property Office, "International Search Report and Written Opinion," issued in International Patent Application No. PCT/CA2011/050544, dated Dec. 28, 2011.
Canadian Intellectual Property Office, "International Search Report and Written Opinion," issued in International Patent Application No. PCT/CA2011/050543, dated Dec. 19, 2011.
Canadian Intellectual Property Office, "International Search Report and Written Opinion," issued in International Patent Application No. PCT/CA2011/050542, dated Dec. 9, 2011.
United States Patent and Trademark Office, "Office Action," issued in U.S. Appl. No. 13/343,403, dated Oct. 25, 2012.
Canadian Intellectual Property Office, "International Search Report and Written Opinion," issued in International Patent Application No. PCT/CA2010/000998, dated Oct. 7, 2010.
Canadian Intellectual Property Office, "International Preliminary Report on Patentability," for International Patent Application No. PCT/CA2010/000998, dated Jul. 27, 2011.
"Prospects for Managed Underground Storage of Recoverable Water," National Research Council, 2008, p. 243.
"Ozone effects on bacteria, molds and viruses—ozone and bacteria destruction" published Dec. 24, 2007, http://web.archive.org/web20071224191320/http://www.ozoneapplications.com/info/ozone_bacteria_mold_viruses.htm.
Richard P. Wenzel, et al., "The Impact of Hospital-Acquired Bloodstream Infections", Emerging Infectious Diseases, vol. 7, No. 2, Mar.-Apr. 2001, pp. 174-177.
Dr. Carsten Matz, et al., "Biofilm Bacteria Protect Themselves with Chemical Weapons", Helmholtz Centre for Infection Research, Bauschweig, reported on Inforniac.com, Jul. 23, 2008.
United States Patent and Trademark Office, "Office Action," issued in U.S. Appl. No. 13/343,403, dated Mar. 25, 2013.
"Amendment after Non-Final Rejection and Notice of Non-Compliant Amendment," filed Feb. 25, 2013 in U.S. Appl. No. 13/343,403 in response to Notice of Non-Compliant Amendment of Feb. 20, 2013, and Non-Final Office Action of Oct. 25, 2012.
"Amendment Under 37 C.F.R. §1.116 With Request for Consideration Under the Final Consideration Pilot Program 2.0," filed Jun. 25, 2013 in U.S. Appl. No. 13/343,403 in response to final Office Action of Mar. 25, 2013.
"Supplemental Amendment," filed Jul. 19, 2013 in U.S. Appl. No. 13/343,403 in response to final Office Action of Mar. 25, 2013 and the telephonic interview of Jul. 19, 2013.
United States Patent and Trademark Office, "Comments on Statement of Reasons for Allowance," filed Sep. 6, 2013 in U.S. Appl. No. 13/343,403 in response to Notice of Allowability dated Aug. 2, 2013.
World Intellectual Property Organization "Amendment Pursuant to Art. 19 of the Patent Cooperation Treaty" for PCT Application No. PCT/CA2010/000998, Dec. 2, 2010, 14 pages, Ottawa, Ontario, Canada.
Canada Intellectual Property Office "Amendment Under Art. 34" issued in to PCT Application No. PCT/CA2010/000998, Mar. 1, 2011, 7 pages, Ottawa, Ontario, Canada.
United States Patent and Trademark Office, "Notice of Allowability" issued in U.S. Appl. No. 13/343,403 dated Aug. 2, 2013.
Canadian Intellectual Property Office, "International Search Report and Written Opinion, " issued in International Patent Application No. PCT/CA2010/001364, dated Dec. 3, 2010.
Patent Cooperation Treaty, "Notification of the Recording of a Change" issued in PCT Application No. PCT/CA/2010/000998 dated Mar. 17, 2011.
Rogers et al., "Bacillus anthracis Spore Inactivation by Fumigant Decontamination", Applied Biosaftey, 2008, vol. 13, No. 2, pp. 89-98, available at http://www.absa.org/abj/abj/081302Rogers.pdf.
United States Environmental Protection Agency, "US Environmental Protection Agency Office of Pesticide Programs List H: EPA's Registered Products Effective Against MRSA and VRE" Jan. 9, 2009.
Whitney et al., "Inactivation of Bacillus anthracis Spores", Emerging Infectious Diseases, Jun. 2003, vol. 9, no. 6, pp. 623-627, available at http://wwwnc.cdc.gov/eid/article/9/6/pdfs/02-0377.pdf.

* cited by examiner

FOOD-HANDLING FACILITY DISINFECTION TREATMENT

CROSS-REFERENCE TO RELATED APPLICATIONS

This application is the national stage under 35 U.S.C. §371 of International Patent Application No. PCT/CA2011/050544, filed Sep. 8, 2011, designating the United States, and published Mar. 15, 2012 as International Publication No. WO/2012/031366, which application claims priority to and the benefit of U.S. Patent Application Ser. No. 61/380,758 filed on Sep. 8, 2010. The disclosures of the above-identified applications are expressly incorporated herein by this reference in their entireties.

FIELD OF THE INVENTION

This invention relates to bacterial disinfection treatments for food handling premises such as food processing rooms, meat packing plants, food packaging rooms, kitchens and the like. More particularly, it relates to processes and systems for methods and systems for disinfecting food handling premises of human-harmful, food poisoning-causing bacteria including *Listeria* species bacteria such as *Listeria monocytogenes* and *Salmonella* species such a *S. typhium*, causative agents of food poisoning in humans and animals.

BACKGROUND OF THE INVENTION

*Listeria* is a genus of Gram-positive bacteria of the bacilli class. It contains six species, typified by *L. monocytogenes*, the causative agent of listeriosis, an uncommon but potentially lethal food-borne infection. *L. monocytogenes* is one of the most virulent food-borne pathogens. Listeriosis has been reported to be the leading cause of death among food-borne bacterial pathogens, responsible for about 2,500 illnesses and 500 deaths annually in the United States.

*L. monocytogenes* is commonly found in soil, stream water, sewage, plants and food. Vegetables can become contaminated with *L. monocytogenes* from the soil. Uncooked meats, unpasteurized milk, products made from unpasteurized milk such as certain cheeses, and processed foods commonly contain *Listeria*. Sufficient heating and cooking will kill *Listeria*, but contamination of food products can occur after cooking and before packaging. Meat processing plants, for example, producing ready-to-eat products such as deli meats and hot dogs, follow extensive sanitation policies to guard against *listeria* contamination.

Outbreaks of *Listeria* have reportedly been caused by hot dogs, deli meats, raw milk, soft-ripened cheeses, raw and cooked poultry, raw meats, ice cream, raw vegetables and raw and smoked fish. Pregnant women, the elderly and those with compromised immune systems are the most vulnerable patients. In its early stages *Listeria* infection is effectively treated with antibiotics such as ampicillin, ciprofloxacin and azithromycin, but it is commonly not recognized until a more advanced stage is reached. Prevention of such infections is accordingly of high importance.

*Salmonella* is a large genus of bacteria, many species of which can cause disease if ingested by humans. *Salmonella* bacteria infections are commonly termed "*Salmonellosis*" and are manifested by diarrhea, vomiting, fever and abdominal cramps (food poisoning). Among the human harmful *Salmonella* species are *S. enteridis* and its sub-species, *S. bongori* and *S. typhi*, the human pathogen of typhoid fever.

BRIEF REFERENCE TO THE PRIOR ART

Effective sanitation of food contact surfaces is necessary to prevent *listeria* or *salmonella* infection. At present, this is done using alcohol as a topical sanitizer. Quaternary ammonium salts are used in combination with alcohol with increased duration Oxidizing agents (chlorine dioxide, peroxides, ethylene oxide, sodium hypochlorite and the like) may be used to clean *Listerium*- or *Salmonella*-contaminated sites, but these are relatively slow-acting. Such clean-up is time-consuming and costly, since the food handling facility must remain out of commission for extended periods of time. Soft and porous fabric surfaces pose a particular problem, since they will harbor live *Listerium* or *Salmonella* bacteria and render them inaccessible to routine liquid or gaseous treatments. It is important that cleaning and sanitizing agents used in food treatment facilities leave no residues which might be harmful if ingested.

Vaporized hydrogen peroxide (VHP) is highly effective as a sanitizing agent when applied to smooth surfaces, but has little or no efficacy on porous materials and is of questionable value against thick biofilms of a nature more characteristic of a food preparation area. Moreover, VHP is very damaging to electronic devices that may be present in the food handling facility.

Once a porous, soft surface such as carpet, drapery, porous material in ceilings and the like becomes impregnated with bacteria, it cannot be effectively disinfected using currently available agents and processes.

Ozone is known to be a powerful anti-bacterial, anti-fungal and anti-viral agent. For over 100 years, it has been used for water purification. It is known to be effective against *Legionella Bacteria, E. coli* and *pseudomonas* populations in such plants.

Canadian Patent 2,491,781 Lynn, issued Jun. 9, 2009, discloses use of a high pressure water stream and a high pressure ozonized water stream for cleaning and sanitizing objects such as surfaces and poultry carcasses.

Canadian Patent 2,473,540 Gibson and Hobbs, issued Dec. 2, 2008, discloses a ventilation system including a duct containing an ultraviolet light source generating ozone in the air stream passing through the duct, the inlet to which is adjacent to a food cooking source, so that purified air is emitted from the cooking environment.

It is an object of the present invention to provide a novel and effective method of treating facilities and objects infected or prone to infection with human-harmful, food poisoning-causing bacteria.

SUMMARY OF THE INVENTION

The present invention provides, from one aspect, a process of combating human-harmful, food poisoning-causing bacteria in an enclosed space and on surfaces therein, which comprises exposing the bacteria in the space to a disinfecting atmosphere which includes ozone at a concentration of 2-350 ppm by weight and hydrogen peroxide at an amount of 0.2-10 wt. %, at a relative humidity of at least 60%, and for a period of at least 30 minutes sufficient for an effective kill of the bacteria; and subsequently removing ozone from the atmosphere, down to 0.04 ppm or less.

Another aspect of the invention provides a portable system for destroying human-harmful, food poisoning-causing bacteria, in rooms and on surfaces and equipment therein, comprising an ozone generator for discharging into the room a gaseous mixture including ozone; an ozone controller adapted to control the amount of discharged ozone; a source of hydrogen peroxide for discharging controlled amounts of hydrogen peroxide into the room; means for discharging the hydrogen peroxide and ozone into the room; humidity adjusting means adapted to increase or decrease the relative humidity of the room during treatment; and an ozone remover adapted to destroy ozone, down to a safe level in the room atmosphere for subsequent human utilization.

BRIEF REFERENCE TO THE DRAWINGS

THE PREFERRED EMBODIMENTS

Preferred ozone amounts for use in the invention are from about 10-350 parts per million in the disinfection atmosphere, more preferably 20-350, or 20-200, or 20-100, or 35-100, or even more preferably 20-90 parts per million in the oxygen/ozone gas mixture, and most preferably 35-80 ppm ozone. Preferred amounts of hydrogen peroxide are the amounts supplied to the disinfecting atmosphere using an aqueous solution containing 0.2-10%, more preferably 0.5-10%, or 0.5-7%, or 0.5-5%, or 1-5%, or 1-3% hydrogen peroxide. In the description below, the peroxide percentages used are sometimes expressed in terms of these solution percentages. The amounts are chosen so that no serious deleterious effects are suffered by other equipment in the treatment room to which the disinfecting atmosphere is supplied. The amount of hydrogen peroxide in the disinfecting atmosphere can be calculated from the volume of aqueous hydrogen peroxide evaporated into the disinfecting atmosphere, the volume of the room being disinfected and the concentration of hydrogen peroxide in the starting solution. Times of exposure of the room and its surface to the disinfecting atmosphere are suitably from 15 minutes to about 120 minutes, preferably from about 60 to about 105 minutes, and most preferably about 90 minutes. These times are constrained to some extent by the need to clear the room of ozone (down to a maximum of 0.04 ppm) following the disinfection phase, and return the room to normal use within a reasonable period of time, with the entire start-to-finish time not exceeding 150 minutes. The ozone removal is an extremely rapid and fully effective process. Both the hydrogen peroxide and the ozone (and any products of interaction between them) should be removed before the room is put back into normal use.

The preferred portable system for destroying human-harmful, food poisoning-causing bacteria according to the present invention includes, as part of its means for discharging the hydrogen peroxide and ozone into the room, a dislodgement system at the outlet end of the discharging means. The dislodgement system allows penetration of carpet, drape and similar porous surfaces in the room, to gain access to concealed/sequestered colonies of the bacteria, and to attack the bacteria protected by a biofilm formed on surfaces in the room and embedding the bacteria and spores therein. The dislodgement system can be manually operated, with operators protected by a hazard suit and mask, or remotely operated or totally automated. It may take the form of one or more outlet jets, with associated manually operable jet pressure controls. It may take the form of a revolving or fixed brush with bristles of appropriate stiffness, alone or in combination with an outlet jet. Any form of dislodgement system effective to disturb the pile of carpet fabrics, upholstery fabrics and the like so as to access the remote parts which might harbor anthrax spores or colonies can be used. This includes non-physical applications such as air jets, ultrasonic energy radio-frequency energy and electromagnetic waves, for example, capable of causing physical disruption and which result in micro-physical movements of fibrous surfaces.

The ozone for use in the present invention can be generated by any known means. In the case of corona or other electrical discharge generation from oxygen, the apparatus of the invention preferably includes a container of medical grade oxygen. The oxygen container can be a standard, pressurized vessel containing medical grade oxygen, of the type commonly found in medical facilities. Oxygen from this container is fed to an ozone generator, where the oxygen is subjected to electrical discharge, normally with high voltage alternating current, to convert small amounts of the oxygen to ozone and produce a gaseous mixture of oxygen and ozone. The quantity of ozone in the mixture is controllable by adjustment of the voltage of the electrical discharge. Suitable ozone generators are known and available commercially. The relative amounts of ozone generated are relatively small, expressed in parts per million (ppm), but such is the power of ozone as a disinfectant, especially in combination with hydrogen peroxide in accordance with this invention, that such small quantities thereof are all that is required.

Alternative forms of ozone generation can be used if preferred. Ultraviolet radiation of appropriate wavelength, incident upon oxygen or air, is one acceptable alternative. In such a system, air from the room itself may be fed into the ozone generating unit to supply the required oxygen for conversion to ozone. Other methods of ozone generation which can be used include photocatalytic reactions, cold plasma, etc.

The relative humidity of the disinfecting atmosphere in the treatment space should be at least 60% and preferably at least 65%, for effective disinfection. To ensure this, one can incorporate a humidifier in the system of the invention, using sterile water from an internal system reservoir to adjust and control the humidity of the issuing gas mixture. In this way, desirable humidity for most effective disinfection is achieved at the point of discharge where dislodgement of a carpet or drapery surface can take place. Since the adjustable humidifier need only increase the humidity of the space to the desirable level, however, it can be placed in any location within the space. In one embodiment, he hydrogen peroxide vapor is applied, in controlled amounts, to the air/water vapor issuing from the humidifier and thus added to the ozone/oxygen containing gas mixture. Alternatively, hydrogen peroxide can be applied to the water used to humidify the target location. Hydrogen peroxide is commercially available as aqueous solutions of standard concentrations of hydrogen peroxide. For use in embodiments of the present invention, a standard solution of known peroxide concentration is suitably diluted down by a fixed volume of distilled water. The peroxide load is standardized based on the known volume of water from the peroxide solution required to raise the relative humidity to the desired extent, e.g. from 40-80%. From this, the amount of hydrogen peroxide in volume % or ppm by volume introduced into the treatment facility can be calculated.

Certain systems according to embodiments of the invention may include a temperature adjuster and controller for the gas mixture. This can be a simple heater/cooler through which either the incident oxygen or the generated oxygen/ozone mixture passes prior to discharge into the room atmosphere. While simple adjustment of the temperature of the room using an external room heating system and thermostat can be effective, it is preferred to adjust the temperature of the issuing gas mixture, for most effective treatment of the carpet and drapery surfaces. The ideal range of temperature for ozone and ozone/hydrogen peroxide decontamination of *Listeria* is 15° C. to 30° C.

Figure 3:
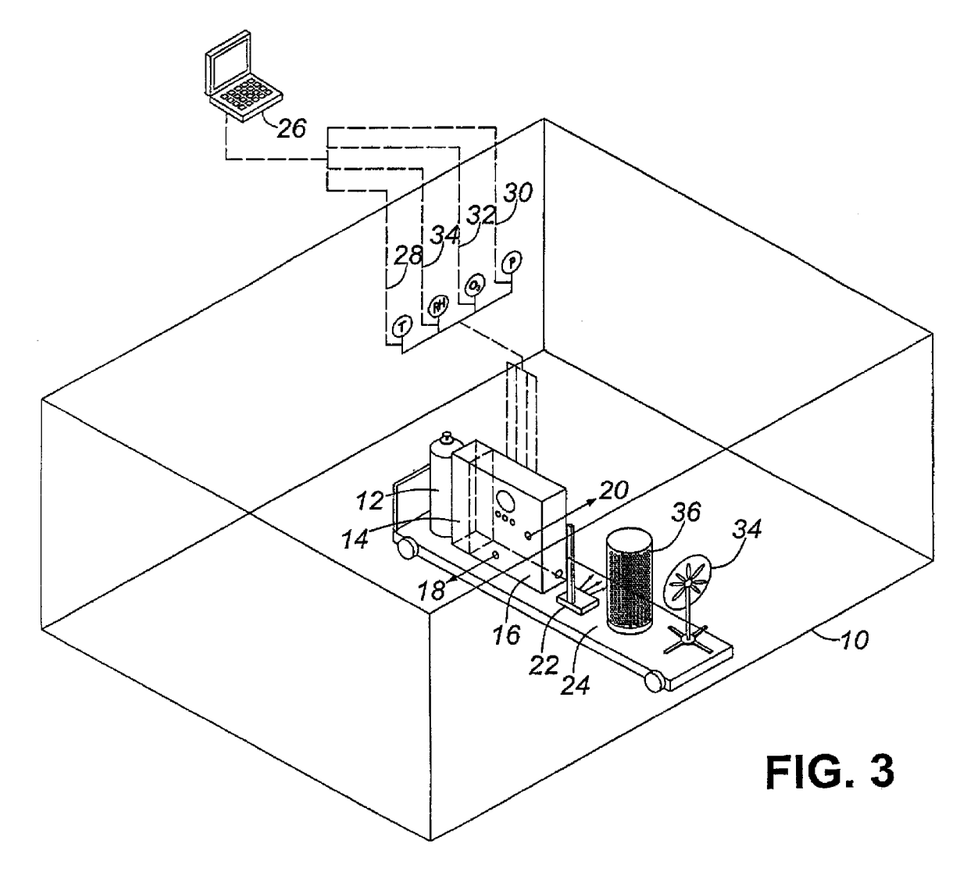
FIG. 3 is a diagrammatic illustration of an apparatus according to the invention, in portable, transportation mode.

The system of the invention also preferably includes an ozone removal unit. Such units are known, and can be purchased commercially for use in the present invention. Depending on the volume of the room atmosphere and the capacity of the ozone removal unit, more than one such unit may be incorporated in the system of the invention. Suitable ozone removal units are those based on activated carbon as the removal medium. These act very quickly, and do not lead to the formation of hazardous reaction products. The inclusion of such units enables the treated facility to be cleared of ozone and returned to normal use rapidly, for economic reasons. Other types include systems based on catalysts such as manganese oxide or other metal oxides, which may be heated to remove moisture, thermal destruction in conjunction with other metals including platinum or palladium.

Human-harmful, food poisoning-causing bacteria to which the present invention is particularly suitable include *Listeria* species such as *Listeria monocytogenes*, and *Salmonella* species such as *S. typhium* and *S. enterides*.

FIG. 1 of the accompanying drawings shows a room 10 such as a room of a food processing facility liable to *Listeria* bacterial contamination and closed ready for disinfection by a process according to an embodiment of the invention. The room is substantially hermetically sealed. Inside the room is a pressurized cylinder 12 of oxygen, feeding oxygen gas into a humidifier 14 and thence to an ozone generator 16, which includes electrical discharge plates of variable voltage to adjust the quantity of ozone which is generated. A heater and a pressure controller (not shown) may be disposed near the entrance to the ozone generator. Output of oxygen/ozone gas mixture is via room outlets 18, 20 to the atmosphere of the room 10, and via wands 22A and/or 22B to a dislodgement means in the form of scrubbing brushes 24A and 24B mounted on the outlet ends of the respective wands 22A, 22B. The heater, the pressure controller, the voltage supplied to the ozone generator 16 and the humidity level supplied by the humidifier 14 are all controlled and adjusted from an external control panel 26 via respective electrical connections 28, 30, 32 and 34. Also disposed within the room is an oscillating fan 34 and an ozone destruct filter unit 36.

Disposed within the room 10 is a container of aqueous hydrogen peroxide solution 19 and associated air blower 21 which, during operation, blows vaporized hydrogen peroxide in controlled amounts into discharge wand 22A and 22B to mix with the output of ozone/oxygen therein. The amount of hydrogen peroxide being supplied is controlled by adjustment of the blower 21 through a connection thereof to the control panel 26. In an alternative arrangement, hydrogen peroxide can be supplied from generator 19 to the humidifier 14.

FIGS. 2A and 2B of the accompanying drawings show in more detail forms of dislodgement means 24A and 24B for use in the present invention, attached to the outlet, discharge ends of respective wands 22. The dislodgement means 24A has a jet outlet nozzle 38A at its extremity, and a generally circular plate 40 mounted on the wand 22A near the discharge end. The wand 22A passes through a central aperture 42 in a plate 40. The plate 40 has brush bristles 46A mounted on its lower surface, arranged in two arcs around the jet outlet nozzle 38A and protruding downwardly to an extent just beyond the extent of outlet from nozzle 38A. In use, oxygen/ozone gas mixture or oxygen/ozone/hydrogen peroxide gas mixture issues from nozzle 38A at relatively high pressure, and can be directed by the operator holding the wand to a carpet surface area while at the same time the operator scrubs the carpet surface area with the bristles 46A.

FIG. 2B shows an alternative but essentially similar arrangement, in which plate 40 is replaced by a wheeled platform 44 carrying two rotary brushes 46B and three gas jet outlets 38B for the oxygen/ozone/hydrogen peroxide delivery at pressure, located forwardly of the rotary brushes 46B.

FIG. 3 of the accompanying drawings illustrates the portability of a system according to the invention. Parts are numbered as in FIG. 1. A 4-wheeled cart 48 is provided, on which all the component parts of the system can be loaded for ease of transportation from one room to another. The instrumentation and control panel can be disconnected for transportation, and re-connected and disposed outside when the apparatus is placed in another room for use as shown in FIG. 1. The cart 48 is removed while the system is in use, but is loaded with the components after use, either for transportation to another room or for storage.

The operation of the system will be readily apparent from the preceding description of its component parts and their inter-connection. The cart 48 carrying the component parts is wheeled into the room 10 to be disinfected, and the parts are distributed around the room and connected together as illustrated in FIG. 1. An operator wearing a hazard suit and other appropriate protective clothing enters the room and holds the wand 22. The room is sealed. Conditions of treatment are set on the control panel 26, and the apparatus is switched on so that oxygen/ozone/hydrogen peroxide gas mixture at controlled ozone concentration, hydrogen peroxide concentration, relative humidity, temperature and elevated pressure issues from jet nozzle 38. The operator applies the jetted gas mixture to the carpet surfaces, drapery surfaces and other absorbent surfaces in the room, scrubbing the surfaces at the same time with the bristles 46. The room becomes pressurized above atmospheric pressure, due to the introduction of the oxygen/ozone gas mixture. Pressure is continually monitored by the control panel 26 to ensure safe working conditions for the operator, as well as the temperature, humidity and ozone concentration in the room. Smooth surfaces in the room may not need the action of the dislodgement means, but are satisfactorily disinfected by contact with the disinfecting atmosphere in the room. The oscillating fan 34 is operated throughout the procedure, to circulate the oxygen/ozone mixture throughout the room.

After a pre-set time of the procedure, and after all the appropriate, absorbent surfaces have been scrubbed, a time not normally exceeding 90 minutes, the hydrogen peroxide supply, the oxygen supply and ozone generator are switched off. Then the ozone destruct filter 36 is operated, sucking in the ozone-containing gases, destroying the ozone and issuing pure oxygen from it. The room can now be opened, the apparatus disconnected and loaded on the cart 48, and the room put back to its normal use.

EXPERIMENTAL EXAMPLES

Figure 4:
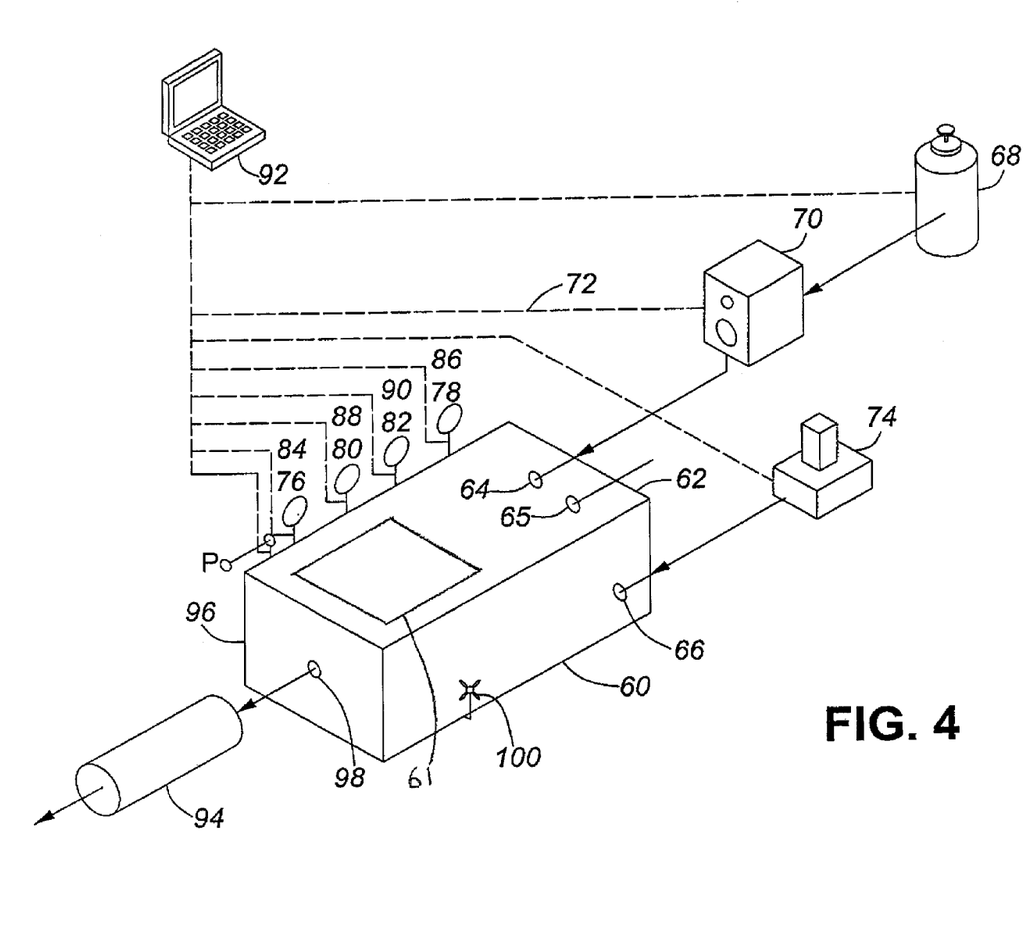
FIG. 4 is a diagrammatic illustration of a test apparatus used to generate some of the test results reported below.

Effective and optimum conditions for use in the present invention were determined using a laboratory apparatus as generally illustrated in FIG. 4 of the accompanying drawings.

A single pure colony of *Listerium monocytogenes* was inoculated to a Columbia agar plate with 5% sheep's blood. They were incubated at 35° C. in room air for 18-24 hours. From the plate, 4-5 isolated colonies were selected, and suspended in tryptic soy broth to achieve a 0.5 McFarland turbidity standard ($1.5 \times 10^8$ cfu/ml) measured using a spectrophotometer. Inoculum was prepared by performing a series of serial dilutions of 0.9 ml 0.85 NaCl broth with 0.1 ml of original 0.5 McFarland inoculum (6×10 fold) to give solutions of $10^{-1}$, $10^{-2}$, $10^{-3}$, $10^{-4}$, $10^{-5}$, $10^{-6}$ and $10^{-7}$ cfu/mL. Incubation of these serially diluted solutions and subsequent counting of the resulting viable colonies determines the dilution at which growth is eliminated, to be expressed as a log kill. Thus, if growth is eliminated at a three-fold ($10^{-3}$ cfu/ml solution), this is a log 3 kill. This is standard procedure.

Organisms were plated out in triplicate, 0.1 ml of each solution being spread over the surface of Columbia sheep's blood agar plates. Two sets of 12 plates were subjected to ozone/oxygen exposure at preselected concentrations of ozone (ppm), humidity and temperature conditions in the illustrated apparatus. The other sets of 2 were treated as controls, with no ozone exposure, but kept at room temperature.

For ozone exposure, the apparatus generally illustrated in FIG. 4 was used.

The test plates were mounted inside a disinfection chamber 60, the upstream end 62 of which had an ozone inlet port 64, a hydrogen peroxide vapor inlet port 65 and a water vapor inlet port 66. A cylinder 68 of pressurized medical grade oxygen was provided, feeding oxygen to an ozone generator 70, equipped with alternating current electrical plates to which variable voltage could be supplied via input control 72. The output of oxygen/ozone mixed gas from the ozone generator 70 was fed to the ozone inlet port 64 of the disinfection chamber 60. A water vapor humidifier 74 supplied water vapor to inlet port 66. The disinfection chamber 60 also contained a heater/cooler (not shown), a temperature sensor 76, a pressure sensor 78, a humidity sensor 80 and an ozone sensor 82, connected electrically via respective lines 84, 86, 88 and 90 to a control panel and monitor 92, connected to feed back to the oxygen cylinder 68 to control flow for pressure adjustment purposes, to the ozone generator 70 to control and adjust the ozone quantity, to the water vapor humidifier 74 to control and adjust relative humidity in the disinfection chamber 60, and to the heater/cooler to control and adjust the temperature in the chamber. These parameters were all pre-set on the control panel to desired values and automatically re-adjusted themselves to these values as the experiments progressed.

An ozone destruct filter 94 was connected to the downstream end 96 of the disinfection chamber 60 at outlet port 98, to destroy ozone issuing from the chamber 60 at the end of the experiment. Gases were circulated within the chamber 60, and expelled therefrom at the termination of the experiment, using a fan 100 mounted therein. After placing the test plates in the chamber 60, it is sealed until the end of each experiment.

In a similar manner, test plates of *Salmonella typhium* were prepared, with the same serial dilutions, and exposed to ozone and hydrogen peroxide according to the invention The control plates and the ozone treated plates were placed in an incubator at the same time. The plate counts were read through a microscope, and the numbers of colony forming units on each plate was counted.

Example 1

Table 1 below provides a summary of experiments, whereby combinations of ozone, $H_2O_2$, humidity and exposure time, at room temperature, were evaluated in terms of the ability to eliminate *Listerium monocytogenesis* and *Salmonella typhium* when artificially applied as a biofilm onto non-porous surfaces namely stainless steel discs. Columns A, B, C and D are the counts at the serial dilutions $10^{-1}$, $10^{-2}$, $10^{-3}$ and $10^{-4}$ respectively.

The steel discs for testing and the agar plates for testing were prepared, exposed and tested as described in the previous Example, in an apparatus generally as illustrated in FIG. 4, with exposure conditions shown in the Table 1 below.

TABLE 1

| Run # | Organism | Ozone (PPM) | H2O2 (%) | EXP (min) | Humidity | Disc | A | B | C | D |
|---|---|---|---|---|---|---|---|---|---|---|
| Control | *Listeria* | 0 | 0 | 0 | 0 | 1 | TNTC | 176 | 12 | 2 |
| Control | *Listeria* | 0 | 0 | 0 | 0 | 2 | TNTC | 123 | 17 | 1 |
| Control | *Listeria* | 0 | 0 | 0 | 0 | 3 | TNTC | 189 | 15 | 0 |
| 1 | *Listeria* | 80 | 1.0% | 30 | 80 | 4 | 0 | 0 | 0 | 0 |
| 1 | *Listeria* | 80 | 1.0% | 30 | 80 | 5 | 0 | 0 | 0 | 0 |
| 1 | *Listeria* | 80 | 1.0% | 30 | 80 | 6 | 0 | 0 | 0 | 0 |
| 2 | *Listeria* | 80 | 1.0% | 45 | 80 | 7 | 0 | 0 | 0 | 0 |
| 2 | *Listeria* | 80 | 1.0% | 45 | 80 | 8 | 0 | 0 | 0 | 0 |
| 2 | *Listeria* | 80 | 1.0% | 45 | 80 | 9 | 0 | 0 | 0 | 0 |
| 3 | *Listeria* | 80 | 1.0% | 60 | 80 | 10 | 0 | 0 | 0 | 0 |
| 3 | *Listeria* | 80 | 1.0% | 60 | 80 | 11 | 0 | 0 | 0 | 0 |
| 3 | *Listeria* | 80 | 1.0% | 60 | 80 | 12 | 0 | 0 | 0 | 0 |
| 4 | *Listeria* | 80 | 1.5% | 60 | 80 | 13 | 0 | 0 | 0 | 0 |
| 4 | *Listeria* | 80 | 1.5% | 60 | 80 | 14 | 0 | 0 | 0 | 0 |
| 4 | *Listeria* | 80 | 1.5% | 60 | 80 | 15 | 0 | 0 | 0 | 0 |
| Control | *Salmonella* | 0 | 0 | 0 | 0 | 1 | TNTC | TNTC | 112 | 26 |
| Control | *Salmonella* | 0 | 0 | 0 | 0 | 2 | TNTC | TNTC | 63 | 9 |
| Control | *Salmonella* | 0 | 0 | 0 | 0 | 3 | TNTC | TNTC | 77 | 4 |
| 1 | *Salmonella* | 80 | 1.0% | 30 | 80 | 4 | 134 | 18 | 1 | 0 |

TABLE 1-continued

| Run # | Organism | Ozone (PPM) | H202 (%) | EXP (min) | Humidity | Disc | A | B | C | D |
|---|---|---|---|---|---|---|---|---|---|---|
| 1 | Salmonella | 80 | 1.0% | 30 | 80 | 5 | 161 | 13 | 0 | 0 |
| 1 | Salmonella | 80 | 1.0% | 30 | 80 | 6 | 112 | 15 | 3 | 0 |
| 1 | Salmonella | 80 | 1.0% | 60 | 80 | 4 | 3 | 0 | 0 | 0 |
| 1 | Salmonella | 80 | 1.0% | 60 | 80 | 5 | 5 | 0 | 0 | 1 |
| 1 | Salmonella | 80 | 1.0% | 60 | 80 | 6 | 1 | 0 | 0 | 0 |

Example 2

Figure 1:
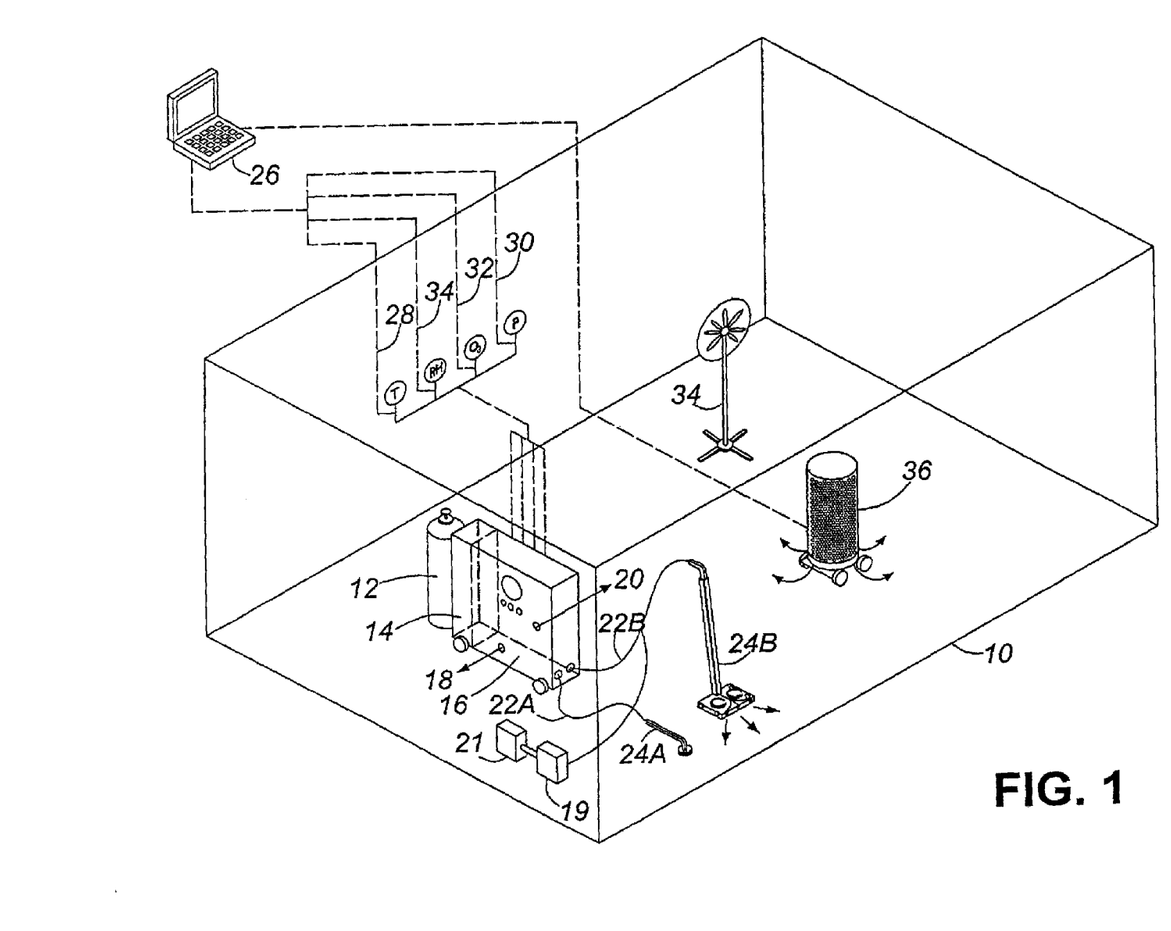
FIG. 1 of the accompanying drawings is a diagrammatic illustration of an apparatus in accordance with an embodiment of the invention, disposed within a room to be disinfected.
Figure 2A:
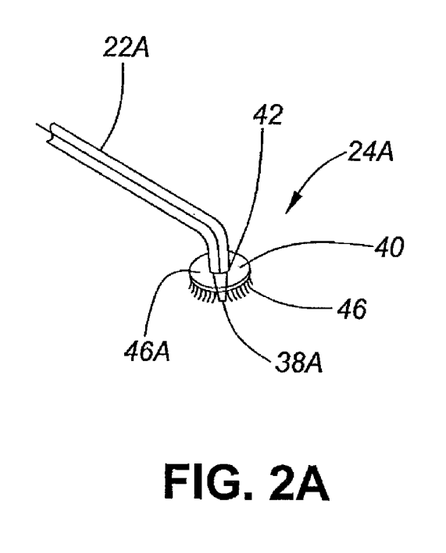
FIGS. 2A and 2B are diagrammatic illustrations of physical agitation systems for use in embodiments of the invention.
Figure 2B:
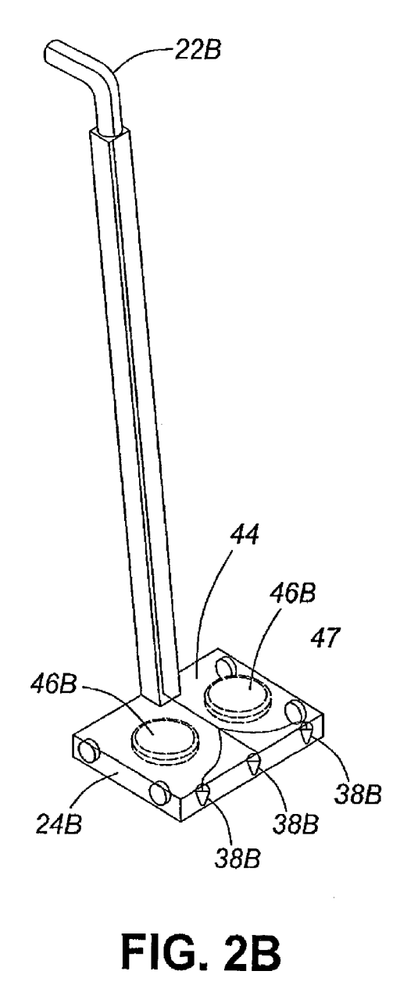

Another series of experiments was conducted with the same *Listeria monocytogenes* strain at room temperature, but deposited onto fibrous carpet samples instead of steel discs. The *Listeria* carrying carpet samples were suspended in a room as generally depicted in accompanying FIG. 1, and the ozone/hydrogen peroxide/water disinfecting atmosphere was blown at the carpet surface with a fan directed at the carpet, causing physical agitation of the fibrous carpet surface. The agar plates for testing were prepared as previously described. Serial dilutions of 10-fold, 100-fold, 1000-fold and 10,000-fold were effected and incubated. In duplicate runs using 80 ppm ozone, 1% hydrogen peroxide and 80% relative humidity, no viable colonies of *Listeria* were detected, at any of the dilutions, whereas control, unexposed but contaminated carpet samples had colonies too numerous to count.

Similarly, in duplicate runs with the same composition of atmosphere for a duration of 45 minutes, no viable colonies of *Listeria* were detected at any of the dilutions.

Example 3

A further set of experiments was conducted using *Listeria* and *Salmonella*, which produced results which demonstrate efficacy at both 60 ppm and 45 ppm ozone with 1% hydrogen peroxide and an exposure time of 30 minutes at room temperature. In these runs the bacteria were exposed within biofilms on stainless steel discs only. This was done to better mimic the type of material normally found in a government approved food preparation area, i.e. since one normally does not find fabrics in such spaces. Should fabrics be present however, preferentially 80 ppm of ozone for at least 30 minutes (depending on the type of carpet present) should be used to achieve a 100% kill.

TABLE 2

| Run # | Organism | Ozone (PPM) | H202 (%) | EXP (min) | Humidity | A | B | C | D |
|---|---|---|---|---|---|---|---|---|---|
| Control | Listeria | 0 | 0 | 0 | 0 | TNTC | 176 | 12 | 2 |
| Control | Listeria | 0 | 0 | 0 | 0 | TNTC | 123 | 17 | 1 |
| Control | Listeria | 0 | 0 | 0 | 0 | TNTC | 189 | 15 | 0 |
| Control | Listeria | 0 | 0 | 0 | 0 | TNTC | 135 | 5 | 0 |
| Control | Listeria | 0 | 0 | 0 | 0 | TNTC | 186 | 9 | 1 |
| 1 | Listeria | 30 | 1.0% | 30 | 80 | 0 | 0 | 0 | 0 |
| 1 | Listeria | 30 | 1.0% | 30 | 80 | 0 | 0 | 0 | 0 |
| 2 | Listeria | 45 | 1.0% | 30 | 80 | 0 | 0 | 0 | 0 |
| 2 | Listeria | 45 | 1.0% | 30 | 80 | 0 | 0 | 0 | 0 |
| 1 | Listeria | 45 | 1.0% | 30 | 80 | 0 | 0 | 0 | 0 |
| 1 | Listeria | 45 | 1.0% | 30 | 80 | 0 | 0 | 0 | 0 |
| 2 | Listeria | 60 | 1.0% | 30 | 80 | 0 | 0 | 0 | 0 |
| 2 | Listeria | 60 | 1.0% | 30 | 80 | 0 | 0 | 0 | 0 |
| 1 | Listeria | 80 | 1.0% | 30 | 80 | 0 | 0 | 0 | 0 |
| 1 | Listeria | 80 | 1.0% | 30 | 80 | 0 | 0 | 0 | 0 |
| 2 | Listeria | 80 | 1.0% | 45 | 80 | 0 | 0 | 0 | 0 |
| 2 | Listeria | 80 | 1.0% | 45 | 80 | 0 | 0 | 0 | 0 |
| 2 | Listeria | 80 | 1.0% | 45 | 80 | 0 | 0 | 0 | 0 |
| Control | Salmonella | 0 | 0 | 0 | 0 | TNTC | 187 | 18 | 1 |
| Control | Salmonella | 0 | 0 | 0 | 0 | TNTC | 86 | 6 | 0 |
| Control | Salmonella | 0 | 0 | 0 | 0 | TNTC | 94 | 3 | 1 |
| Control | Salmonella | 0 | 0 | 0 | 0 | TNTC | 193 | 18 | 0 |
| Control | Salmonella | 0 | 0 | 0 | 0 | TNTC | 203 | 16 | 0 |
| Control | Salmonella | 0 | 0 | 0 | 0 | TNTC | 172 | 19 | 2 |
| 1 | Salmonella | 30 | 1.0% | 30 | 80 | 0 | 0 | 0 | 0 |
| 1 | Salmonella | 30 | 1.0% | 30 | 80 | 0 | 0 | 0 | 0 |
| 2 | Salmonella | 45 | 1.0% | 30 | 80 | 0 | 0 | 0 | 0 |
| 2 | Salmonella | 45 | 1.0% | 30 | 80 | 0 | 0 | 0 | 0 |
| 1 | Salmonella | 45 | 1.0% | 30 | 80 | 0 | 0 | 0 | 0 |
| 1 | Salmonella | 45 | 1.0% | 30 | 80 | 0 | 0 | 0 | 0 |
| 2 | Salmonella | 60 | 1.0% | 30 | 80 | 0 | 0 | 0 | 0 |
| 2 | Salmonella | 60 | 1.0% | 30 | 80 | 0 | 0 | 0 | 0 |
| 1 | Salmonella | 80 | 1.0% | 30 | 80 | 0 | 0 | 0 | 0 |
| 1 | Salmonella | 80 | 1.0% | 30 | 80 | 0 | 0 | 0 | 0 |
| 2 | Salmonella | 80 | 1.0% | 45 | 80 | 0 | 0 | 0 | 0 |
| 2 | Salmonella | 80 | 1.0% | 45 | 80 | 0 | 0 | 0 | 0 |
| 2 | Salmonella | 80 | 1.0% | 45 | 80 | 0 | 0 | 0 | 0 |

What is claimed is:

1. A process of combating human-harmful, food poisoning-causing bacteria and spores thereof in an enclosed space and on surfaces within the space, consisting of:
    exposing the bacteria in the space and on surfaces therein to a disinfecting atmosphere which includes ozone at an amount of 2-350 ppm by weight and hydrogen peroxide at an amount of 0.5-10 wt. %, at a relative humidity of at least 60%, and for a period of at least 30 minutes sufficient for an effective kill of the bacteria and spores; wherein the amount of hydrogen peroxide is derived from a supply solution of 0.2%-10% hydrogen peroxide; and subsequently removing ozone from the atmosphere, down to 0.04 ppm or less.

2. The process of claim 1 wherein the amount ozone in the disinfecting atmosphere is from 10-350 ppm.

3. The process of claim 2 wherein the amount ozone in the disinfecting atmosphere is from 20-200 ppm.

4. The process of claim 1 wherein the amount ozone in the disinfecting atmosphere is from 20-100 ppm.

5. The process of claim 2 wherein the amount ozone in the disinfecting atmosphere is from 35-100 ppm.

6. The process of claim 1, wherein the hydrogen peroxide amount in the disinfecting atmosphere is from 0.5-7%.

7. The process of claim 6, wherein the hydrogen peroxide amount in the disinfecting atmosphere is from 1-5%.

8. The process of claim 1, wherein the period of exposure is from about 30 minutes to about 120 minutes.

9. The process of claim 8, wherein the period of exposure is from about 60 minutes to about 105 minutes.

10. The process of claim 1, wherein exposing the bacteria in the space occurs while subjecting porous and fibrous surfaces within the space to physical agitation while exposed to the disinfecting atmosphere.

11. The process of claim 10 wherein the physical agitation is conducted with application of bristles.

12. The process of claim 10 wherein the physical agitation is conducted with application of air pressure jets.

13. The process of claim 10 wherein the physical agitation is conducted with application of ultrasonic energy, radio frequency energy or electromagnetic waves, capable of causing physical disruption.

14. The process of claim 1, wherein biofilm carrying surfaces are exposed to a localized stream of the disinfecting atmosphere.

15. The process of claim 14 wherein the localized stream is provided at a pressure of from 14.7 to 100 psi.

16. The process of claim 1, wherein the bacteria is a *Listeria* species.

17. The process of claim 16, wherein the *Listeria* species is *Listeria monocytogenes*.

18. The process of claim 1, wherein the bacteria is a *Salmonella* species.

19. The process of claim 18, wherein the *Salmonella* species is either *Salmonella typhimurium* or *Salmonella typhi*.

* * * * *